(12) United States Patent  
Cawley et al.

(10) Patent No.: US 10,561,456 B2  
(45) Date of Patent: Feb. 18, 2020

(54) BONE SCREW INCORPORATING A POROUS SURFACE FORMED BY AN ADDITIVE MANUFACTURING PROCESS

(71) Applicant: RENOVIS SURGICAL TECHNOLOGIES, INC., Redlands, CA (US)

(72) Inventors: Trace Cawley, Boca Raton, FL (US); Thomas Ross, Austin, TX (US)

(73) Assignee: KYOCERA Medical Technologies, Inc., Redlands, CA (US)

( * ) Notice: Subject to any disclaimer, the term of this patent is extended or adjusted under 35 U.S.C. 154(b) by 86 days.

(21) Appl. No.: 15/044,499

(22) Filed: Feb. 16, 2016

(65) Prior Publication Data

US 2016/0157908 A1 Jun. 9, 2016

Related U.S. Application Data

(63) Continuation-in-part of application No. 14/504,509, filed on Oct. 2, 2014, now Pat. No. 10,154,913, and (Continued)

(51) Int. Cl.  
*A61B 17/86* (2006.01)  
*A61F 2/30* (2006.01)  
(Continued)

(52) U.S. Cl.  
CPC ........ *A61B 17/866* (2013.01); *A61B 17/7032* (2013.01); *A61B 17/7035* (2013.01); *A61B 17/8625* (2013.01); *A61F 2/0077* (2013.01); *A61F 2/3094* (2013.01); *A61F 2/30771* (2013.01); *A61F 2002/0081* (2013.01); (Continued)

(58) Field of Classification Search  
CPC .. A61F 2002/30011; A61F 2002/30013; A61F 2002/30911; A61F 2002/3093; A61F 2310/00796; A61F 2/0077  
See application file for complete search history.

(56) References Cited

U.S. PATENT DOCUMENTS 6,139,550 A 10/2000 Michelson  
7,272,855 B1 9/2007 Yemeni et al.  
(Continued)

OTHER PUBLICATIONS

Dec. 1, 2014 International Search Report issued in International Patent Application No. PCT/US14/47940.  
(Continued)

*Primary Examiner* — Samuel S Hanna  
(74) *Attorney, Agent, or Firm* — Clements Bernard Walker; Christopher L. Bernard (57) ABSTRACT

The present invention provides a bone screw or bone anchor, such as a threaded pedicle screw or the like, incorporating a porous surface for enhancing bony fixation, ingrowth, and purchase when implanted in bone. Preferably, this porous surface covers at least a portion of the threads of the bone screw or bone anchor. The porous surface is formed by a conventional or novel additive manufacturing process, such as three-dimensional (3D) printing or the like, optionally as well as a prior and/or subsequent machining process. The porous surface may include novel needle-like protrusions and/or lattice structures, and/or any other protruding/depressed features, whether regular or irregular.

8 Claims, 6 Drawing Sheets

Related U.S. Application Data a continuation-in-part of application No. 14/339,508, filed on Jul. 24, 2014.

(51) Int. Cl.
*B33Y 80/00* (2015.01)
*A61B 17/70* (2006.01)
*A61F 2/00* (2006.01)
*B33Y 10/00* (2015.01)

(52) U.S. Cl.
CPC ............ *A61F 2002/3092* (2013.01); *A61F 2002/3093* (2013.01); *B33Y 10/00* (2014.12); *B33Y 80/00* (2014.12)

(56) References Cited

U.S. PATENT DOCUMENTS

| | | | |
|---|---|---|---|
| 8,496,710 B2 | 7/2013 | Bagga et al. | |
| 8,920,868 B2* | 12/2014 | Stephan | A61C 8/0012 |
| | | | 427/2.26 |
| 2007/0225785 A1 | 9/2007 | Park et al. | |
| 2007/0233071 A1* | 10/2007 | Dewey | A61B 17/7001 |
| | | | 606/250 |
| 2008/0161927 A1* | 7/2008 | Savage | A61F 2/4455 |
| | | | 623/17.16 |
| 2009/0326671 A1 | 12/2009 | Schofield | |
| 2010/0298950 A1 | 11/2010 | McDonnell et al. | |
| 2012/0277869 A1 | 11/2012 | Siccardi et al. | |
| 2013/0056912 A1 | 3/2013 | O'Neill et al. | |
| 2013/0264749 A1* | 10/2013 | Jones | G06F 17/50 |
| | | | 264/497 |
| 2013/0310948 A1* | 11/2013 | Luscher | A61B 17/68 |
| | | | 623/23.58 |

OTHER PUBLICATIONS

Jan. 7, 2015 International Search Report issued in International Patent Application No. PCT/US2014/058759.

* cited by examiner

FIG. 6

BONE SCREW INCORPORATING A POROUS SURFACE FORMED BY AN ADDITIVE MANUFACTURING PROCESS

CROSS-REFERENCE TO RELATED APPLICATIONS

The present patent application/patent is a continuation-in-part (CIP) of co-pending U.S. patent application Ser. No. 14/339,508, filed on Jul. 24, 2014, and entitled "SURGICAL IMPLANT DEVICES INCORPORATING POROUS SURFACES," and U.S. patent application Ser. No. 14/504,509, filed on Oct. 2, 2014, and entitled "SURGICAL IMPLANT DEVICES INCORPORATING POROUS SURFACES AND A LOCKING PLATE," the contents of all of which are incorporated in full by reference herein.

FIELD OF THE INVENTION

The present invention relates generally to a surgical implant device. More specifically, the present invention relates to a bone screw incorporating a porous surface for enhancing bony fixation, ingrowth, and purchase when implanted in bone. This porous surface is formed by a conventional or novel additive manufacturing process, optionally as well as a prior and/or subsequent machining process. The porous surface may include novel needle-like protrusions and/or lattice structures, and/or any other protruding/depressed features, whether regular or irregular.

BACKGROUND OF THE INVENTION

A variety of conventional pedicle screws are known to those of ordinary skill in the art. These pedicle screws typically consist of a threaded screw portion including an enlarged head and a head body, or tulip. The threaded screw portion engages a pedicle of a vertebra of the spine, and the head body engages the head of the threaded screw portion, optionally by passing the threaded screw portion through a hole manufactured into the bottom portion of the head body until the head is seated in or adjacent to the bottom portion of the head body, for example. Other coupling configurations may also be used. The pedicle screws can be monoaxial or polyaxial, allowing the head body multiple degrees of freedom with respect to the threaded screw portion. Once placed, rods are inserted into the head bodies of adjacent pedicle screws and set screws are placed to simultaneously secure the head bodies to their respective threaded screw portions and to lock the rods in place. A rigid framework is thereby formed, suitably stabilizing and fixing the vertebrae of the spine in a predetermined alignment. Although a pedicle screw is illustrated and described herein, it will be readily apparent to those of ordinary skill in the art that the principles of the present invention apply equally to other types of bone screws and bone anchors.

When various surgical implant devices, well known to those of ordinary skill in the art, disposed in or placed adjacent to bony surfaces, it is desirable that adequate friction is present to hold them in place and that surfaces are available for bony fixation, ingrowth, and purchase over time. Accordingly, these surgical implant devices often incorporate mechanically-manufactured friction surfaces formed by conventional subtractive manufacturing processes, or utilize friction coatings or bondings for such purposes. However, these mechanically-manufactured friction surfaces, typically consisting of teeth, grooves, striations, or the like, are often not adequate and do little to promote bony fixation, ingrowth, and purchase. Similarly, these friction coatings or bondings may delaminate and fail over time.

Thus, what are still needed in the art are improved bone screws and bone anchors that incorporate essentially-integral friction surfaces that are strong and durable, and that provide adequate surface area for bony fixation, ingrowth, and purchase, while still being economical to manufacture. Improved additive and pre and post-processing manufacturing processes now make this possible.

BRIEF SUMMARY OF THE INVENTION

In various exemplary embodiments, the present invention provides a bone screw or bone anchor, such as a threaded pedicle screw or the like, incorporating a porous surface for enhancing bony fixation, ingrowth, and purchase when implanted in bone. Preferably, this porous surface covers at least a portion of at least some of the threads of the bone screw or bone anchor. The porous surface is formed by a conventional or novel additive manufacturing process, such as three-dimensional (3D) printing or the like, optionally as well as a prior and/or subsequent machining process. Thus, for example, the entire bone screw, including the porous surface, may be additively manufactured; a base bone screw may be conventionally manufactured and then the porous surface may be additively manufactured on top of the base bone screw; and/or the bone screw, including the porous surface, may be additively manufactured and then the porous surface may be conventionally machined or otherwise surface modified. For example, a cylindrical blank may be 3D printed, including both a solid portion and a porous portion, and then threads and other geometry may be manufactured from this cylindrical blank. The key aspect is that the porous surface is additively manufactured, as opposed to using a conventional subtractive manufacturing process, such as machining or etching, or other coating or bonding process. The porous surface may include novel needle-like protrusions and/or lattice structures, and/or any other protruding/depressed features, whether regular or irregular.

In one exemplary embodiment, the present invention provides a bone screw, comprising: a threaded shaft portion; a head portion coupled to the threaded shaft portion; a tapered or narrowed tip portion coupled to the threaded shaft portion opposite the head portion; and one or more threads disposed concentrically about the threaded shaft portion, wherein at least some of the one or more threads comprise a porous surface. Optionally, intermediate spaces disposed between the one or more threads also comprise the porous surface. Optionally, at least a portion of the head portion also comprises a porous surface. Optionally, at least a portion of the tapered tip portion also comprises a porous surface. The porous surface is additively manufactured by building up raised areas of the porous surface that protrude relative to depressed areas of the porous surface that are not built up. Optionally, one or more of the threaded shaft portion, the head portion, and the tapered tip portion are additively manufactured. Optionally, the porous surface comprises regular raised portions. Alternatively, the porous surface comprises irregular raised portions.

In another exemplary embodiment, the present invention provides a method for manufacturing a bone screw, comprising: one or more of subtractively and additively forming a shaft; one or more of subtractively and additively forming one or more threads disposed concentrically about the shaft; and additively manufacturing a porous surface on at least a portion of at least some of the one or more threads. The method also includes one or more of subtractively and additively forming a head coupled to the shaft. The method further includes one or more of subtractively and additively forming a tapered or narrowed tip coupled to the shaft. Optionally, the method further includes subtractively modifying one or more of the shaft, the one or more threads, and the porous surface. Optionally, the porous surface comprises regular raised portions. Alternatively, the porous surface comprises irregular raised portions. The porous surface is additively manufactured by building up raised areas of the porous surface that protrude relative to depressed areas of the porous surface that are not built up.

BRIEF DESCRIPTION OF THE DRAWINGS

The present invention is illustrated and described herein with reference to the various drawings, in which like reference numbers are used to denote like device components/method steps, as appropriate, and in which:

FIG. 5 is a flowchart illustrating one exemplary embodiment of the method of the present invention, wherein the entire bone screw, including the porous surface, is additively manufactured, with or without subsequent conventional machining or the like; and FIG. 6 is a flowchart illustrating another exemplary embodiment of the method of the present invention, wherein a base bone screw is conventionally manufactured and then the porous surface is additively manufactured on top of the base bone screw, with or without subsequent conventional machining or the like.

DETAILED DESCRIPTION OF THE INVENTION

Again, in various exemplary embodiments, the present invention provides a bone screw or bone anchor, such as a threaded pedicle screw or the like, incorporating a porous surface for enhancing bony fixation, ingrowth, and purchase when implanted in bone. Preferably, this porous surface covers at least a portion of at least some of the threads of the bone screw or bone anchor. The porous surface is formed by a conventional or novel additive manufacturing process, such as 3D printing or the like, optionally as well as a prior and/or subsequent machining process. Thus, for example, the entire bone screw, including the porous surface, may be additively manufactured; a base bone screw may be conventionally manufactured and then the porous surface may be additively manufactured on top of the base bone screw; and/or the bone screw, including the porous surface, may be additively manufactured and then the porous surface may be conventionally machined or otherwise surface modified. For example, a cylindrical blank may be 3D printed, including both a solid portion and a porous portion, and then threads and other geometry may be manufactured from this cylindrical blank. The key aspect is that the porous surface is additively manufactured, as opposed to using a conventional subtractive manufacturing process, such as machining or etching, or other coating or bonding process. The porous surface may include novel needle-like protrusions and/or lattice structures, and/or any other protruding/depressed features, whether regular or irregular.

Figure 1:
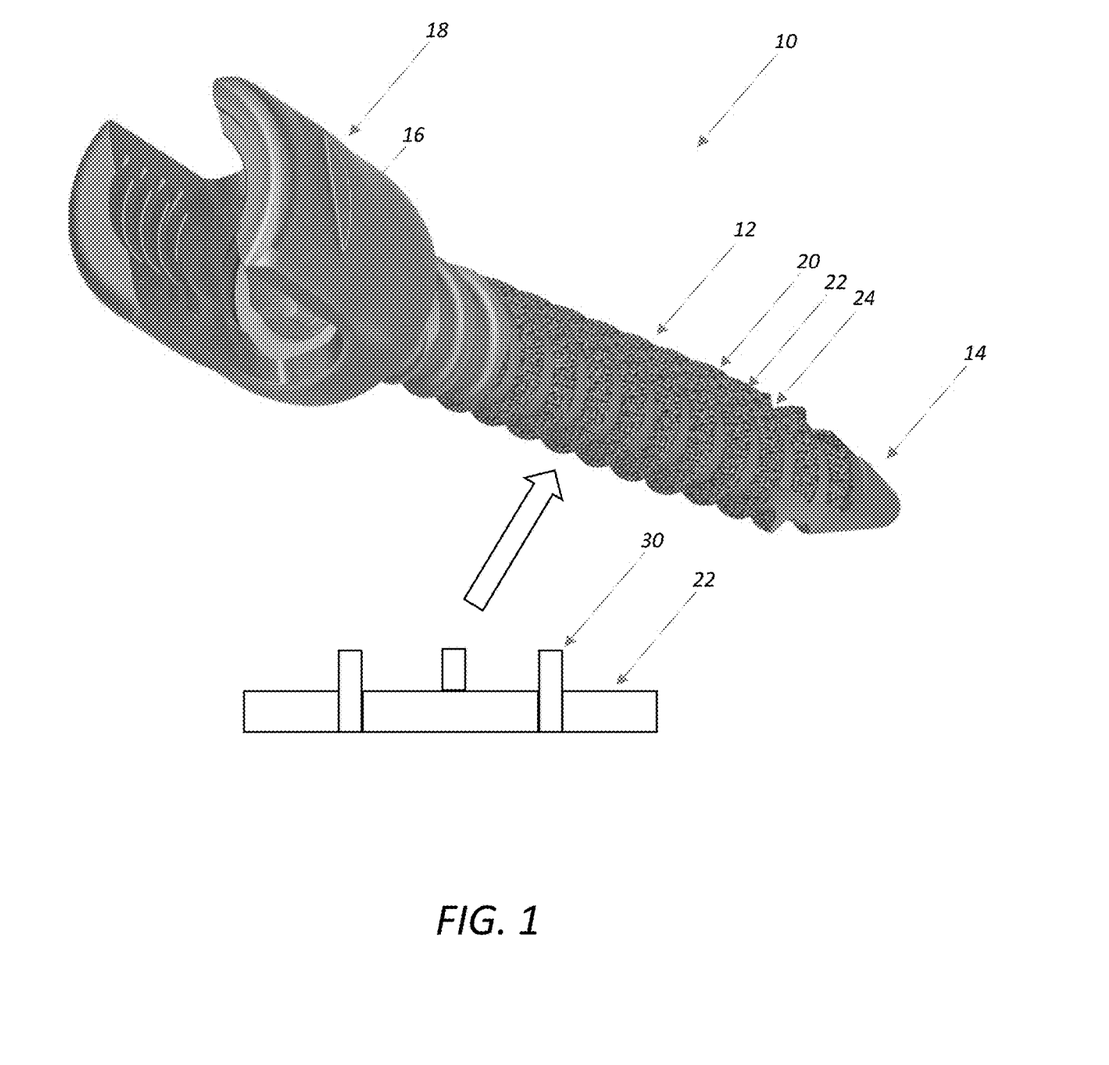
FIG. 1 is a perspective view of an exemplary pedicle screw incorporating a porous surface formed by an additive manufacturing process, the porous surface covering at least a portion of the raised threaded portion of the pedicle screw.
Figure 2:
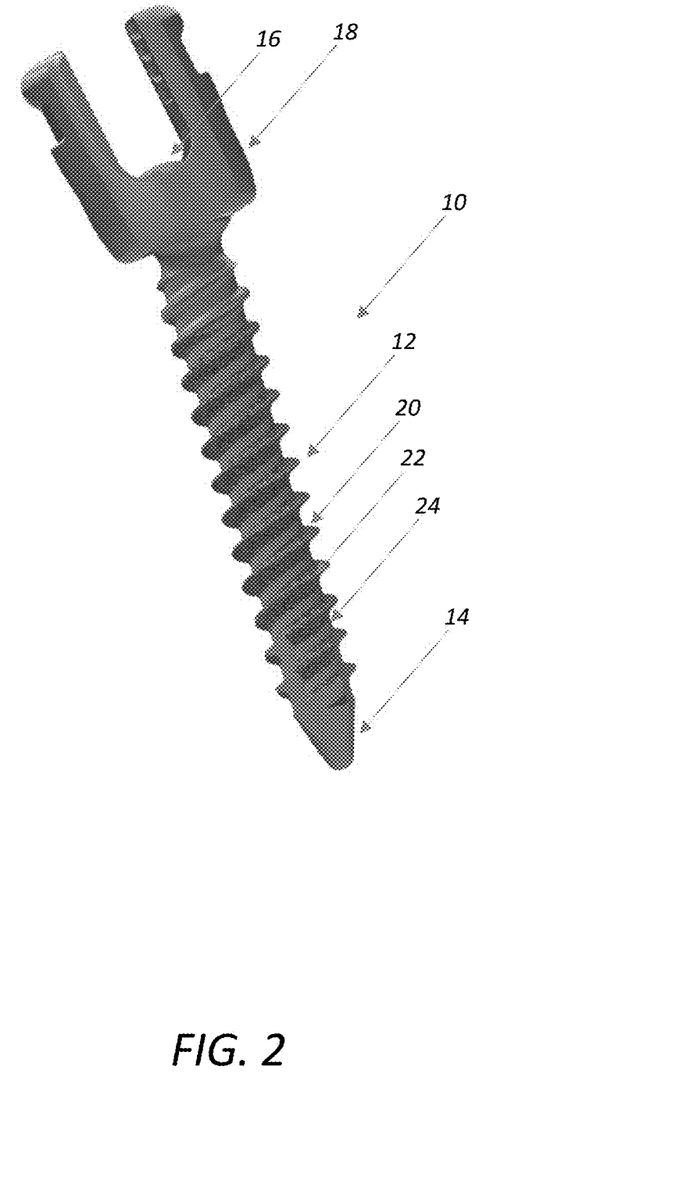
FIG. 2 is a planar view of an exemplary pedicle screw incorporating a porous surface formed by an additive manufacturing process, the porous surface covering at least a portion of the raised threaded portion of the pedicle screw.

Referring now specifically to FIGS. 1 and 2, in one exemplary embodiment, the bone screw 10 of the present invention includes a threaded shaft portion 12 including a tapered tip portion 14 and a head portion 16. In this exemplary embodiment, a pedicle screw is provided. Thus, a head body 18, or tulip, is selectively coupled to the head portion 16, although it will be readily apparent to those of ordinary skill in the art that the principles of the present invention apply equally to all types of bone screws and bone anchors. The threaded shaft portion 12 includes one or more raised threads 20, which may be single-lead threads, dual-lead threads, or multi-lead threads, as desired in a given application. The one or more raised threads 20 are configured to selectively engage bony material. Accordingly, at least some of the one or more raised threads 20 include a porous surface 22 that promotes bony fixation, ingrowth, and purchase. In this exemplary embodiment, at least some of the one or more raised threads 20 include the porous surface 22, while the intermediate spaces 24 between the one or more raised threads 20 do not, nor do the tip portion 14 or the head portion 16 of the bone screw 10. For example, proximal threads 20 may not include the porous surface 22 such that the overall bone screw 10 has greater strength in use. It will be readily apparent to those of ordinary skill in the art that any additional portions may also be covered by the porous surface 22.

Figure 3:
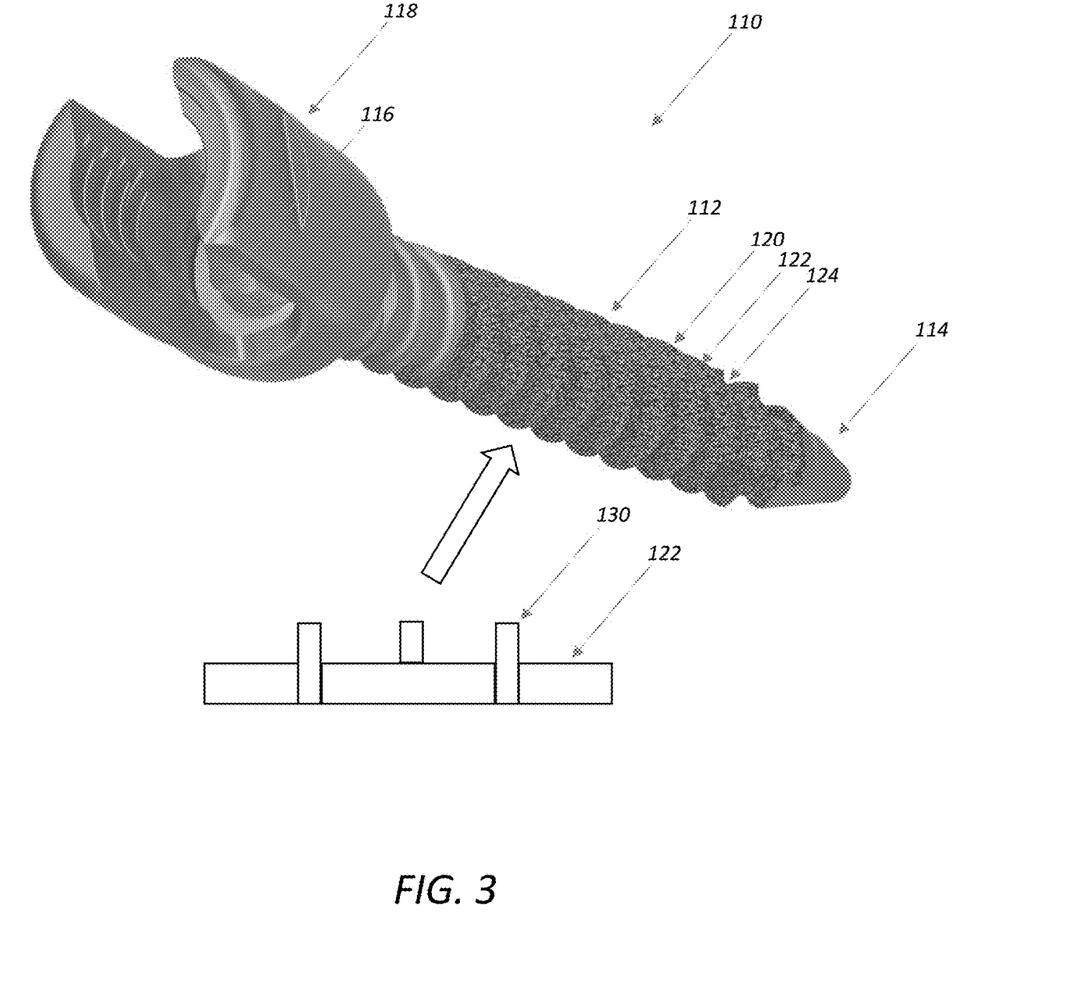
FIG. 3 is a perspective view of an exemplary pedicle screw incorporating a porous surface formed by an additive manufacturing process, the porous surface covering at least a portion of the entire threaded portion of the pedicle screw.
Figure 4:
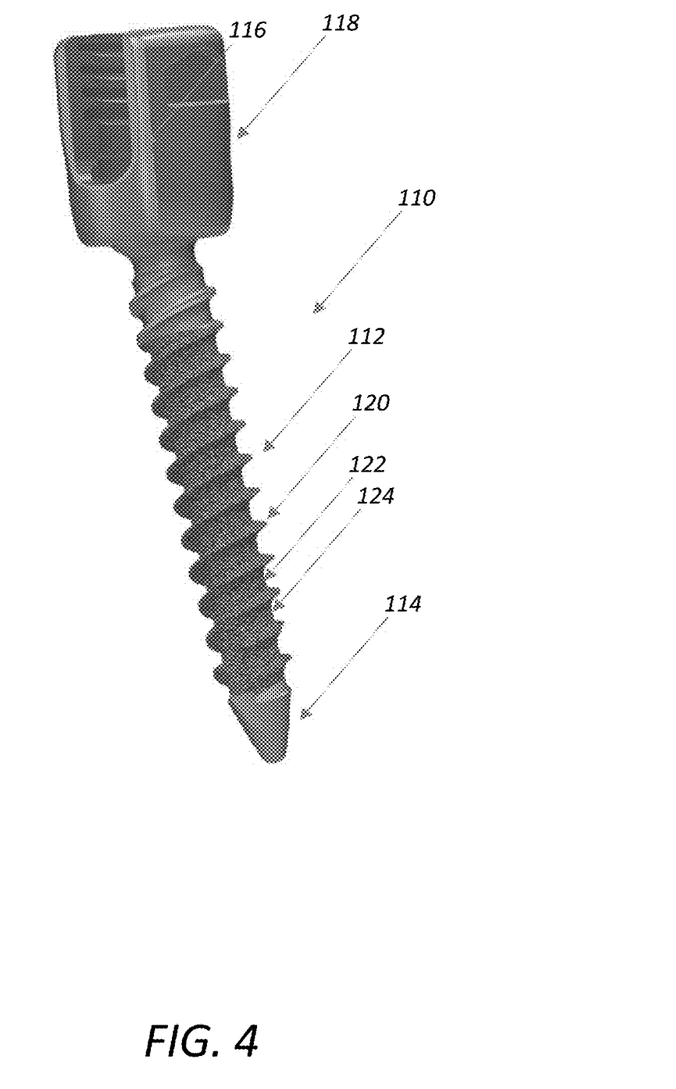
FIG. 4 is a planar view of an exemplary pedicle screw incorporating a porous surface formed by an additive manufacturing process, the porous surface covering at least a portion of the entire threaded portion of the pedicle screw.

Referring now specifically to FIGS. 3 and 4, in another exemplary embodiment, the bone screw 110 of the present invention includes a threaded shaft portion 112 including a tapered tip portion 114 and a head portion 116. In this exemplary embodiment, a pedicle screw is again provided. Thus, a head body 118, or tulip, is selectively coupled to the head portion 116, although it will be readily apparent to those of ordinary skill in the art that the principles of the present invention apply equally to all types of bone screws and bone anchors. The threaded shaft portion 112 includes one or more raised threads 120, which may be single-lead threads, dual-lead threads, or multi-lead threads, as desired in a given application. The one or more raised threads 120 are configured to selectively engage bony material. Accordingly, at least some of the one or more raised threads 120 include a porous surface 122 that promotes bony fixation, ingrowth, and purchase. In this exemplary embodiment, the one or more raised threads 120 include the porous surface 122, along with the intermediate spaces 124 between the one or more raised threads 120, while the tip portion 114 and the head portion 116 of the bone screw 110 do not. It will again be readily apparent to those of ordinary skill in the art that any additional portions may also be covered by the porous surface 122.

Figure 5:
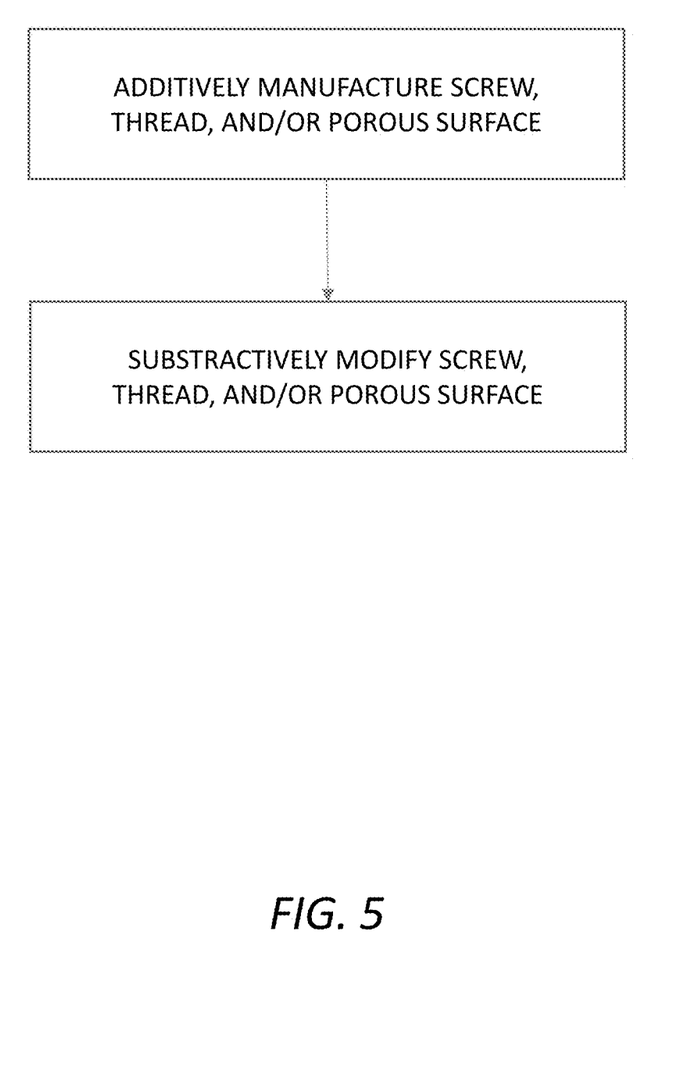
Figure 6:
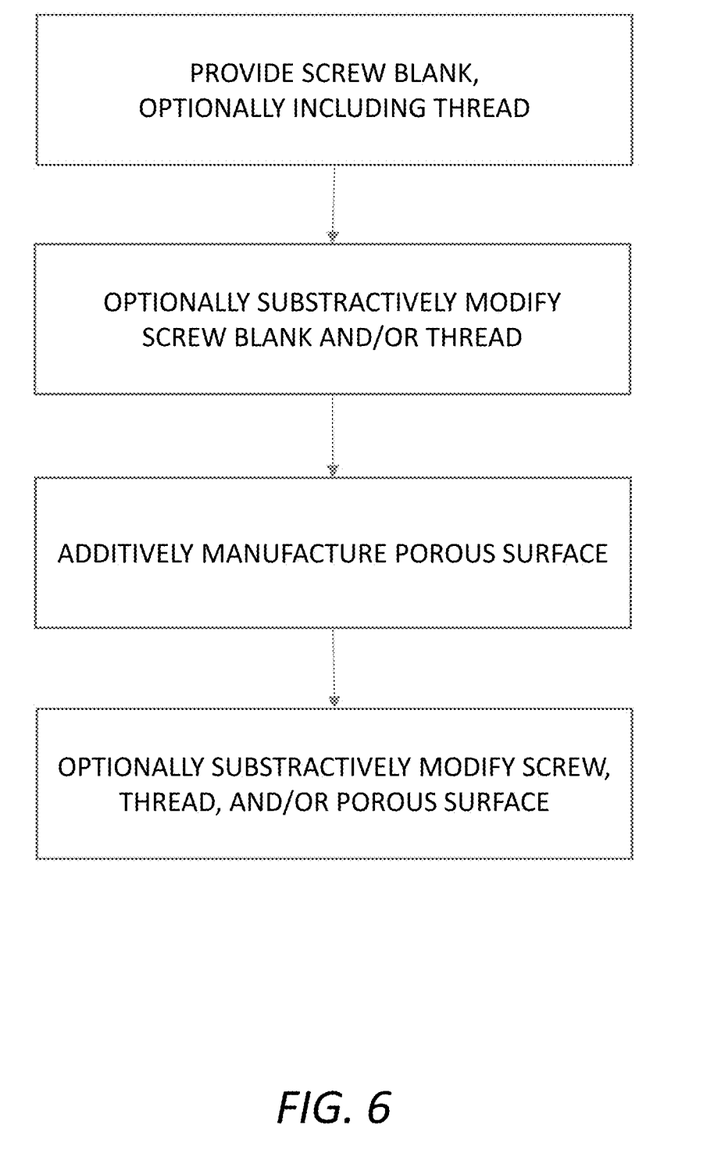

Referring now specifically to FIGS. 5 and 6, in two exemplary embodiments, the porous surface is formed by a conventional or novel additive manufacturing process, such as 3D printing or the like, optionally as well as a prior and/or subsequent machining process. Thus, for example, referring to FIG. 5, the entire bone screw, including the porous surface, may be additively manufactured. Alternatively, referring to FIG. 6, a base bone screw may be conventionally manufactured and then the porous surface may be additively manufactured on top of the base bone screw. Referring to FIGS. 5 and 6, the bone screw, including the porous surface, may be additively manufactured and then the porous surface may be conventionally machined or otherwise surface modified. The key aspect is that the porous surface is additively manufactured, as opposed to using a conventional subtractive manufacturing process, such as machining or etching, or other coating or bonding process. The porous surface may include novel needle-like protrusions and/or lattice structures, and/or any other protruding/depressed features, whether regular or irregular.

Generally speaking, and without intending to be limiting, one aspect of the invention relates to a bone screw or bone anchor 10, 100 that includes, for example, at least the following: a primary structure formed from metal and at least one needle-populated or otherwise textured metallic surface portion 22, 122 formed on at least one exterior portion of the primary structure, the at least one surface portion 22, 122 located such that it engages with a patient's bone when the implant 10, 100 is implanted in the patient. Such needle-populated, metallic surface portions 22, 122 may contain, for example, a collection of at least fifty, a hundred, two hundred, five-hundred or more needles 30, 130, and may be further characterized by at least one, two, three, four, five or more of the following characteristics: (a) the needles 30, 130 in the collection are all oriented substantially normal to the surface portion 22, 122; (b) the needles 30, 130 in the collection are all oriented in substantially the same direction, with the direction being other than normal to the surface portion 22, 122; (c) the needles 30, 130 in the collection are all oriented in substantially the same direction, with the direction being other than normal to the surface portion 22, 122, but within 15 degrees from the normal direction; (d) the needles 30, 130 in the collection are all oriented in substantially the same direction, with the direction being other than normal to the surface portion 22, 122, and more than 15 degrees from the normal direction; (e) the collection includes needles 30, 130 oriented in at least three different directions relative to the surface portion 22, 122; (f) the collection includes needles 30, 130 oriented in at least five different directions relative to the surface portion 22, 122, with all of the needles 30, 130 oriented within 20 degrees from the surface portion 22, 122 normal direction; (g) all of the needles 30, 130 in the collection have substantially the same height; (h) the collection includes needles 30, 130 of at least three different heights; (i) all of the needles 30, 130 in the collection have substantially the same shape; (j) the collection includes needles 30, 130 of at least two different shapes; (k) the needles 30, 130 are distributed substantially uniformly over the surface portion 22, 122; (l) the needles 30, 130 are distributed non-uniformly over the surface portion 22, 122; (m) all of the needles 30, 130 in the collection are anchored to the primary structure; (n) most of the needles 30, 130 in the collection are anchored to the primary structure; (o) most of the needles 30, 130 in the collection are anchored to structural elements contained within an osteo-porous, osteo-derived or trabecular coating 22, 122 on the at least one exterior portion of the primary structure; and/or (p) all of the needles 30, 130 in the collection are anchored to structural elements contained within an osteo-porous, osteo-derived or trabecular coating 22, 122 on the at least one exterior portion of the primary structure. The at least one exterior portion preferably includes at least one osteo-porous surface 22, 122, which may comprise at least one osteo-derived surface 22, 122. The at least one osteo-porous surface 22, 122 and the needles 30, 130 may be simultaneously formed by an additive manufacturing process, such as, but not limited to, EBM or DMSLS.

Again, generally speaking, and without intending to be limiting, another aspect of the invention relates to method(s) for making a medical implant with at least one osteo-porous surface by, for example: forming at least a portion of a primary structure of the implant and forming at least one needle-populated metallic surface portion on at least one exterior portion of the primary structure using an additive manufacturing technique, the at least one needle-populated surface portion located such that it engages with a patient's bone when the implant is implanted in the patient.

The exemplary flow starts with a spongy bone sample, which is micro CT scanned to obtain 3D scan data, which is then processed into solid model data representing an osteo-porous or osteo-derived texture. This texture data is then combined with data representing the overall implant geometry to create a fabrication file for use by either of the manufacturing steps that follow.

The fabrication file may utilize any recognizable solid model specification, such as ".amf" format or ".stl" format, and may be embodied on any sort of permanent storage medium (e.g., CD, CD-ROM, flash memory), semi-permanent (e.g., SRAM) or transitory (e.g., DRAM) storage medium, or embodied in a coded data signal.

Additional background details concerning the fabrication of medical devices using additive techniques can be found in: J. Vehvilainen, "Process and Web Application Development of Medical Applications of Additive Manufacturing," Master's Thesis, Aalto University, School of Science, Dec. 27, 2011 (incorporated by reference and available at http://lib.tkk.fi/Dipl/2011/urn100592.pdf (accessed Jun. 13, 2012)).

An additional step can be inserted that adds outwardly-protruding "needles" on the outer surface(s) of the osteo-porous and/or osteo-derived coating(s). Such needles substantially increase the coefficient of friction of the coating. Having a high coefficient of friction is clinically advantageous because it provides stronger initial fixation, which is important before bone is able to grow onto/into the porous structure. Such needles can be uniformly or non-uniformly distributed along the porous surface. Likewise, various shapes for the needles are possible, including rectangular, pyramidal, conical, tube-shaped, etc. Also, the needles need not be oriented exactly normal to the exterior surface, but are preferably oriented in a substantially normal (e.g., within +/−15 degrees from normal) orientation. Furthermore, the orientation and/or shape of all needles need not be the same, and the needles may be rendered on selected portions, or the entirety, of the exterior coated surface(s).

Two preferred process flows for fabricating and finishing implants using an abrasive blast are provided. Two alternative flows that employ the blasting technique are provided as well. The non-blasted samples are mostly smooth if viewed on a 20 or 100 μm scale, whereas the blasted samples are almost entirely rough, when viewed at similar magnification. This blast process creates a texture approximately 1-20 μm in scale. This is an ideal scale for microtexture because it helps osteoblasts adhere to the titanium struts. The base material is not deposited on the strut (as an HA coating would be). It simply textures the titanium surface by erosion.

In accordance with the invention, the preferred abrasive blast process utilizes an MCD Apatitic Abrasive (Multi-phased Calcium Phosphate containing HA, TCP and other CaP phases) distributed by Hitemco Medical Applications, Inc., 160 Sweet Hollow Rd., Old Bethpage, N.Y. 11804. The blast media has a 425-180 μm size range. The process utilizes a Comco AccuFlo® standard tank micro-abrasive blaster, equipped with Simoom® Technology and Powder-Gate® valve. Tank orifice is 0.40 inches; Nozzle is 0.060 inches; Pressure is 90+/−5 psi. A satisfactory roughness has been achieved when the blast does not further affect the visual appearance, specifically the color and reflectivity of the device. Machined devices may require a blast touch up.

Slightly-irregular lattices are ideally adapted for additive manufacturing. Node perturbation refers to the location of intersecting struts. In accordance with this aspect of the invention, such intersection locations are randomized such that the node deviates from a uniform lattice by a randomized distance. Strut size randomization refers to a deviation in cross-section dimension (e.g., strut diameter). Discrete struts in a lattice could have different cross-sectional sizes, or the struts could have a diameter gradient from one end to the other. These parameters can be randomized for greater diversity in the lattice's geometry. Such slightly-irregular lattices can be used to fabricate any sort of medical implant for which regular lattices are currently used, including, for example, those disclosed in the incorporated Pressacco et al. and Jones et al. applications.

It should be understood that the novel structures disclosed and enabled by the present invention are not limited exclusively to those manufactured using additive manufacturing. Indeed, as persons skilled in the art will appreciate, other known surface modification techniques—such as, for example, Surfi-Sculpt (U.S. Pat. No. 7,667,158, incorporated by reference herein)—may be used to produce the osteoporous, osteo-derived, and/or needle-containing textures of the inventive implants.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A bone screw, comprising:
    a threaded shaft portion;
    a head portion coupled to the threaded shaft portion;
    a tip portion coupled to the threaded shaft portion opposite the head portion; and
    one or more threads disposed concentrically about the threaded shaft portion, wherein at least some of the one or more threads comprise a base and a porous surface coupled to the base, said porous surface comprising a lattice structures comprising intersecting struts;
    wherein the porous surface is formed to approximate a scanned three-dimensional spongy bone surface and comprises a plurality of needles, wherein: (1) some of the plurality of needles are relatively longer needles and are anchored both directly to the base and directly to the intersecting struts of the porous surface and (2) some intervening of the plurality of needles are relatively shorter than the relatively longer needles and are anchored directly only to the intersecting struts of the porous surface and not directly to the base, and being spaced apart from the base;
    wherein the plurality of needles comprise at least two different shapes and are disposed in at least two different orientations with respect to the base; and
    wherein any external portions of the porous surface and the plurality of needles are microtextured.

2. The bone screw of claim 1, wherein intermediate spaces disposed between the one or more threads also comprise the porous surface.

3. The bone screw of claim 1, wherein at least a portion of the head portion also comprises a porous surface.

4. The bone screw of claim 1, wherein at least a portion of the tip portion also comprises a porous surface.

5. The bone screw of claim 1, wherein the porous surface is additively manufactured by building up raised areas of the porous surface that protrude relative to depressed areas of the porous surface that are not built up.

6. The bone screw of claim 1, wherein one or more of the threaded shaft portion, the head portion, and the tip portion are additively manufactured.

7. The bone screw of claim 1, wherein the porous surface comprises regular raised portions.

8. The bone screw of claim 1, wherein the porous surface comprises irregular raised portions.

\* \* \* \* \*